United States Patent [19]

Onozawa et al.

[11] Patent Number: 6,162,533

[45] Date of Patent: Dec. 19, 2000

[54] HARD COAT SHEET CONTAINING AN ANTIBACTERIAL AGENT

[75] Inventors: Yutaka Onozawa; Satoru Shoshi; Shunpei Watanabe, all of Saitama, Japan

[73] Assignee: Lintec Corporation, Tokyo, Japan

[21] Appl. No.: 09/139,561

[22] Filed: Aug. 25, 1998

[30] Foreign Application Priority Data

Aug. 27, 1997 [JP] Japan ................................ 9-246035

[51] Int. Cl.⁷ ............................... B32B 5/16; A01N 1/00
[52] U.S. Cl. ..................... 428/323; 424/443; 428/327; 428/343; 523/122
[58] Field of Search ............................. 428/323, 327, 428/343; 523/122; 424/443

[56] References Cited

U.S. PATENT DOCUMENTS

| | | | |
|---|---|---|---|
| Re. 32,299 | 12/1986 | Randklet ................................ 501/59 |
| 5,213,801 | 5/1993 | Sakuma et al. ....................... 424/429 |
| 5,614,568 | 3/1997 | Mawatari et al. .................... 523/122 |
| 5,770,637 | 6/1998 | Vanderlaan et al. ................. 523/106 |
| 5,967,714 | 10/1999 | Ottersbach et al. ................ 408/404.2 |
| 6,013,275 | 1/2000 | Konagaya et al. ................... 424/443 |

*Primary Examiner*—H. Thi Le
*Attorney, Agent, or Firm*—Armstrong, Westerman, Hattori, McLeland & Naughton

[57] ABSTRACT

A hard coat sheet comprises a transparent base sheet, and a radiation-curing acrylate coat layer including an antibacterial agent provided on the transparent base sheet. Thus, the hard coat sheet has excellent transparency and antibacterial property together with an excellent scratch resistance property.

8 Claims, No Drawings

HARD COAT SHEET CONTAINING AN ANTIBACTERIAL AGENT

BACKGROUND OF THE INVENTION

1. Field of the Invention

The present invention relates to a hard coat sheet (a scratch resistant sheet) having an antibacterial property, and more particularly, to a hard coat sheet having an antibacterial property and an excellent transparency.

2. Description of the Related Art

In recent years, articles having an antibacterial property for foods and for daily life are being increased. These articles includes an antibacterial agent incorporated therein, and the transparency of the article is particularly not required.

There is no prior art article having an antibacterial property and excellent transparency. Especially, there is hitherto no anti-scattering film for a window pane or no film particularly effective for a display such as a display picture.

SUMMARY OF THE INVENTION

Accordingly, it is an object of the present invention to provide a hard coat sheet having an antibacterial property, which can be utilized for an anti-scattering film for a window pane, or, a display such as a display picture.

It has been found from studies made by present inventors that an antibacterial hard coat sheet having an excellent persistency along with a transparency can be produced by blending an antibacterial agent, particularly, an inorganic antibacterial agent into a radiation-curing acrylate.

To achieve the above object, according to a first aspect and feature of the present invention, there is provided a hard coat sheet comprising a transparent base sheet, and a radiation-curing acrylate coat layer including an antibacterial agent provided on the transparent base sheet.

According to a second aspect and feature of the present invention, in addition to the first feature, the weight ratio of the radiation-curing acrylate to the antibacterial agent is in a range of 100:0.1 to 100:15.

According to a third aspect and feature of the present invention, in addition to the first or second feature, the average particle size of the antibacterial agent is equal to or smaller than 1 $\mu$m.

According to a fourth aspect and feature of the present invention, in addition to any of the first to third features, the antibacterial agent is an inorganic substance.

According to a fifth aspect and feature of the present invention, in addition to any of the first to fourth features, an adhesive agent layer is provided on one side of the transparent base sheet.

Thus, a hard coat sheet according to the present invention has excellent transparency and antibacterial property together with an excellent scratch resistance property.

DETAILED DESCIPTION OF THE PREFERRED EMBODIMENT

Examples of the transparent base sheets which may be used are resin films such as polyethylene terephthalate, polycarbonate, polyethylene naphthalate, polypropylene, polyvinyl chloride, polyethylene, polymethylmethacrylate, polyacrylonitrile, triacetyl cellulose and the like.

The base sheet is required to be transparent and may be colored or non-colored. For example, when the hard coat sheet is used as a light shielding film for a window, the base sheet may be selectively colored and transparent, depending upon the type of an application.

It is preferable that the thickness of the base sheet is on the order of 16 to 250 $\mu$m.

The radiation-curing acrylate is particularly not limited, if it is a radiation-curing acrylic resin such as an urethane acrylate, a polyester acrylate, propylene glycoldi (meth) acrylate, pentaerythritol tri (meth) acrylate, trimethylol propane tri(meth)acrylate, dipentaerythritol penta (meth) acrylate, dipentaerythritol hexa (meth) acrylate, hexane dioldi (meth) acrylate, ethylene glycol di (meth) acrylate, diacrylate of ethylene oxide-modified bisphenol A and the like.

When electron beam is used as the radiation, a hardened coating can be formed without addition of a polymerization initiator.

When ultraviolet ray is used as the radiation, a satisfactory hardened coating can be also formed by adding any of the following substances as a photopolymerization initiator: 2-methyl-[4-(methylthio) phenyl]-2-morpholino-1-propanon (Irgacure 907 made by Ciba-Geigy Co.) and 1-hydroxycyclohexylpheny ketone (Irgacure 184 made by Ciba-Geigy Co.). Other photopolymerization initiators can be used such as benzophenone, acetophenone, benzoin, benzoinmethyl ether, benzoinethyl ether, benzoinisopropyl ether, benzoinisobutyl ether, benzoinbenzoic acid, benzoinmethyl benzoate, benzoindimethyl ketal, 2,4-diethylthioxanthene, benzyl diphenyl sulfide, tetramethylthiuram monosulfide, azobisisobutyl nitrile, benzyl, dibenzyl, diacetyl, $\beta$-chloroanthraquinone and the like.

In this case, it is preferable that the blending proportion is 1 to 10 parts by weight based on 100 parts by weight of the radiation-curing acrylate. This is because if the proportion is less than 1 part by weight, the polymerization initiating effect is not obtained, and if the proportion exceeds 10 parts by weight, the yellowing degree is larger to yellow the hard coat sheet, and the durability is also reduced.

If the amount of antibacterial agent incorporated is less than 0.1 part by weight based on 100 parts by weight of the radiation-curing acrylate, the antibacterial property is not obtained. If the amount of antibacterial agent incorporated exceeds 15 parts by weight, the transparency is reduced. Therefore, it is required that the ratio of the radiation-curing acrylate to the antibacterial agent is in a range of 100:0.1 to 100:15.

Particularly, if the average particle size of the antibacterial agent is equal to or smaller than 1 $\mu$m, a hard coat sheet having an excellent transparency can be produced. The reason why it is preferable that the average particle size of the antibacterial agent is equal to or smaller than 1 $\mu$m is that when the antibacterial agent having an average particle size exceeding 1 $\mu$m is used, the dispersability of the antibacterial agent is degraded, resulting in a reduced transparency.

The antibacterial agents which may be used include various antibacterial agents, e.g., inorganic antibacterial agents such as an inorganic antibacterial agent carried on zirconium phosphate, an inorganic antibacterial agent carried on calcium phosphate, an inorganic antibacterial agent carried on silica gel, an inorganic antibacterial agent carried on zeolite, an inorganic antibacterial agent carried on magnesium aluminate meta-silicic acid, and an inorganic antibacterial agent carried on a glass powder; amino acid-based organic antibacterial agents such as an organic antibacterial agent containing an amino acid compound incorporated therein; nitrogen-containing sulfur-based organic antibacterial agents such as an organic antibacterial agent containing a nitrogen-containing sulfur-based compound incorporated therein; and the like. The antibacterial agent may be incorporated in the resin composition in a proper amount adapted to the used type, the antibacterial property and the retention time. Further, a hard coat sheet having an excellent transparency and a long retention time of the antibacterial property can be particularly produced by blending an inorganic antibacterial agent among these antibacterial agents.

If desired, any of additives maybe contained in the resin composition, such as a light stabilizer, an ultraviolet absorbent, a catalyst, a colorant, an anti-static agent, a lubricant, a leveling agent, an anti-foaming agent, a polymerization promoter, an anti-oxidant, a flame retardant, an infrared absorbent, a surfactant, a surface modifier and the like.

A hard coat sheet also having an anti-fouling property can be produced by blending 0.1 to 100 parts by weight of any of the following radiation-curing silicone resin, based on 100 parts of the radiation-curing acrylate: resins of a radical addition type containing alkenyl and mercapto groups; a hydrosilylating reaction type containing an alkenyl group and hydrogen atom; a cation polymerization type containing an epoxy group, a radical polymerization type containing a (meth)acrylate, and the like.

To form the coat layer, a procedure is employed which comprises preparing the resin composition containing 0.1 to 15 parts by weight of an antibacterial agent based on 100 parts by weight of the radiation-curing acrylate resin, coating the resin composition on the base sheet by any coating process such as a gravure coating, a Meyer bar coating and the like, and as required, irradiating ultraviolet rays to the resin composition. In this manner, the cured coating can be formed simply and in an extremely short time.

It is generally preferable that the coat layer is formed at a thickness in a range of 1.5 to 5 $\mu$m. This is because if the thickness is less than 1.5 $\mu$m, the property of hardness is not obtained, and if the thickness exceeds 5 $\mu$m, the antibacterial property is not obtained.

If an adhesive layer is provided on a back of the transparent base sheet having the coat layer formed thereon, the resulting hard coat sheet can be adhered to window panes for a building and a vehicle, and any other objects requiring an abrasion resistance, a wear resistance and an antibacterial property. This is convenient.

The adhesives include, for example, natural rubbers, synthetic rubbers, acrylic resins, polyvinyl ether resins, urethane resins, silicone resins and the like. Particular examples of the synthetic rubbers are styrene-butadiene rubber, polyisobutylene rubber, isobutylene-isoprene rubber, isoprene rubber, styrene-isoprene block copolymer, styrene-butadien block copolymer, styrene-ethylene-butylene block copolymer and the like. Particular examples of the acrylic resins are homopolymers and copolymers of acrylic acid, methyl acrylate, ethyl acrylate, propyl acrylate, butyl acrylate, 2-ethylhexyl acrylate, ethyl methacrylate, butyl methacrylate, acrylo-nitrile and the like. Particular examples of the polyvinyl ether resins are polyvinyl ether, polyvinyl isobutyl ether and the like. Particular examples of the silicone resins are dimethyl polysiloxane and the like.

These adhesives may be used alone or in combination of two or more thereof.

If required, a tackifier, a filler, a softening agent, an anti-oxidant, an ultraviolet absorbent, a cross linking agent and/or the like can be further incorporated in the adhesive. The tackifiers include rosin-based resins, terpene phenol resins, terpene resins, organic hydrocarbon-modified terpere resins, petroleum resins, coumarone-indene resins, styrene-based resins, phenol resin, xylene resin and the like. Fillers include zinc flower, titanium oxide, silica, calcium carbonate, barium sulfate and the like. The softening agents include a process oil, liquid rubbers, a plasticizer and the like. The anti-oxidants include anilide-based, phenol-based, phosphite-based, thioester-based substances and the like. The ultraviolet absorbents include benzophenone-based, benzotriazol-based substances and the like. The cross linking agents include epoxy-based, isocyanate-based, a metal chelate-based substances and the like.

The thickness of the adhesive layer may be usually in a range of 5 to 100 $\mu$m, preferably, 10 to 50 $\mu$m. To protect the adhesive surface, it is preferable that a release sheet is laminated thereon. Further, in the hard coat sheet according to the present invention, the base sheet may be subjected to a printing, and the coat layer or the adhesive layer may be provided, or if required, the adhesive layer may be subjected to a printing. The solvent for the coating agent is particularly not limited, but a solvent having a strong polarity, e.g., methylethyl ketone or isopropyl alcohol is preferred.

EXAMPLES

Examples of the present invention will be described below along with comparative examples.

All of the following incorporated amounts will be represented by part by weight, unless they will be particularly specified.

Example 1

A polyethylene terephthalate film (A4100 made by TOYOBO Co., Ltd.) having a thickness of 50 $\mu$m was used as the base sheet, and a coating agent having the following composition was applied at a thickness of 3 $\mu$m onto the base sheet by a Meyer bar.

Pentaerythritol triacrylate 100

(tri-functional acrylate)

(Aronix M-305 made by Toagosei Co., Ltd.)

Silver-based inorganic antibacterial agent carried on zirconium phosphate 0.1

(having an average particle size of 0.5 $\mu$m)

(NOVARON AG300 made by Toagosei Co., Ltd.)

2-methyl-[4-(methylthio) phenyl]-2-morpholino-1-propane (photopolymerization initiator) 4

(Irgacure 907 made by Ciba-Geigy Co.)

Methylethyl ketone 100

After application of the coating agent, 150 mJ/cm$^2$ of ultraviolet rays were irradiated to the coating agent to provide a hard coat sheet having an excellent antibacterial property.

Example 2

A polyethylene terephthalate film (A4100 made by TOYOBO Co., Ltd.)having a thickness of 50 $\mu$m was used as the base sheet, and a coating agent having the following composition was applied at a thickness of 3 $\mu$m onto the base sheet by the Meyer bar.

Polyester acrylate 100

(tri or more-functional acrylate)

(Aronix M-8060 made by Toagosei Co., Ltd.)

Silver-based inorganic antibacterial agent carried on zirconium phosphate 1

(having an average particle size of 0.5 μm)
(NOVARON AG300 made by Toagosei Co., Ltd.)
2-methyl-[4-(methylthio) phenyl]-2-morpholino-1-propane (photopolymerization initiator) 4
(Irgacure 907 made by Ciba-Geigy Co.)
Isopropyl alcohol 100

After application of the coating agent, 150 mJ/cm$^2$ of ultraviolet rays were irradiated to the coating agent to provide a hard coat sheet having an excellent antibacterial property.

Example 3

A polyethylene terephthalate film (A4100 made by TOYOBO Co., Ltd.) having a thickness of 50 μm was used as the base sheet, and a coating agent having the following composition was applied at a thickness of 3 μm onto the base sheet by the Meyer bar.

Pentaerythritol triacrylate 100
(tri-functional acrylate)
(Aronix M-305 made by Toagosei Co., Ltd.)
Silver-based inorganic antibacterial agent carried on zirconium phosphate 15
(having an average particle size of 0.5 μm)
(NOVARON AG300 made by Toagosei Co., Ltd.)
2-methyl-[4-(methylthio) phenyl]-2-morpholino-1-propane (photopolymerization initiator) 4
(Irgacure 907 made by Ciba-Geigy Co.)
Methylethyl ketone 100

After application of the coating agent, 150 mJ/cm$^2$ Of ultraviolet rays were irradiated to the coating agent to provide a hard coat sheet having an excellent antibacterial property.

Example 4

A polyethylene terephthalate film (A4100 made by TOYOBO Co., Ltd.) having a thickness of 50 μm was used as the base sheet, and a coating agent having the following composition was applied at a thickness of 3 μm onto the base sheet by the Meyer bar.

Pentaerythritol triacrylate 100
(tri-functional acrylate)
(Aronix M-305 made by Toagosei Co., Ltd.)
Silver-based inorganic antibacterial agent carried on calcium phosphate 1
(having an average particle size of 0.3 μm)
(Apasider Clear made by Sangi Co., Ltd.)
2-methyl-[4-(methylthio) phenyl]-2-morpholino-1-propane (photopolymerization initiator) 4
(Irgacure 907 made by Ciba-Geigy Co.)
Methylethyl ketone 100

After application of the coating agent, 150 mJ/cm$^2$ of ultraviolet rays were irradiated to the coating agent to provide a hard coat sheet having an excellent antibacterial property.

Then, an acrylic adhesive agent was applied at a thickness of 20 μm to a surface of the hard coat sheet opposite from the hard coating agent layer by a roll knife coater. After drying of the acrylic adhesive agent, the side subjected to a silicone release treatment of a release film made by subjecting a polyethylene terephthalate to the silicone release treatment was adhered to the side having the acrylic adhesive layer of the hard coat sheet to provide an adhesive sheet.

Example 5

A polyethylene terephthalate film (A4100 made by TOYOBO Co., Ltd.) having a thickness of 50 μm was used as the base sheet, and a coating agent having the following composition was applied at a thickness of 3 μm onto the base sheet by the Meyer bar.

Pentaerythritol triacrylate 100
(tri-functional acrylate)
(Aronix M-305 made by Toagosei Co., Ltd.)
Silver-based inorganic antibacterial agent carried on silica gel 1
(having an average particle size of 0.7 μm)
(Pentanone SZ-U made by Paint Hause Co., Ltd.)
2-methyl-[4-(methylthio) phenyl]-2-morpholino-1-propane (photopolymerization initiator) 4
(Irgacure 907 made by Ciba-Geigy Co.)
Methylethyl ketone 100

After application of the coating agent, 150 mJ/cm$^2$ of ultraviolet rays were irradiated to the coating agent to provide a hard coat sheet having an excellent antibacterial property.

Example 6

A polyethylene terephthalate film (A4100 made by TOYOBO Co., Ltd.) having a thickness of 50 μm was used as the base sheet, and a coating agent having the following composition was applied at a thickness of 3 μm onto the base sheet by the Meyer bar.

Pentaerythritol triacrylate 100
(tri-functional acrylate)
(Aronix M-305 made by Toagosei Co., Ltd.)
Silver-based inorganic antibacterial agent carried on zeolite 1
(having an average particle size of 0.5 μm)
(Zeomic SW1OD made by Sinanen Zeomic Co., Ltd.)
2-methyl-[4-(methylthio) phenyl]-2-morpholino-1-propane (photopolymerization initiator) 4
(Irgacure 907 made by Ciba-Geigy Co.)
Methylethyl ketone 100

After application of the coating agent, 150 mJ/cm$^2$ ultraviolet rays were irradiated to the coating agent to provide a hard coat sheet having an excellent antibacterial property.

Example 7

A polyethylene terephthalate film (A4100 made by TOYOBO Co., Ltd.) having a thickness of 50 μm was used as the base sheet, and a coating agent having the following composition was applied at a thickness of 3 μm onto the base sheet by the Meyer bar.

Pentaerythritol triacrylate 100
(tri-fu nctional acrylate)
(Aronix M-305 made by Toagosei Co., Ltd.)
Silver-based inorganic antibacterial agent carried on magnesium aluminate meta-phosphate 1
(having an average particle size of 0.3 μm)
(AIS-NAZ 310 made by Catalysts & Chemicals Ind Co., Ltd.)
2-methyl-[4-(methylthio) phenyl]-2-morpholino-1-propane
(photopolymerization initiator) 4
(Irgacure 907 made by Ciba-Geigy Co.)

Methylethyl ketone 100

After application of the coating agent, 150 mJ/cm² Of ultraviolet rays were irradiated to the coating agent to provide a hard coat sheet having an excellent antibacterial property.

Example 8

A polyethylene terephthalate film (A4100 made by TOYOBO Co., Ltd.) having a thickness of 50 μm was used as the base sheet, and a coating agent having the following composition was applied at a thickness of 3 μm onto the base sheet by the Meyer bar.

Pentaerythritol triacrylate 100
(tri-functional acrylate)
(Aronix M-305 made by Toagosei Co., Ltd.)
Amino acid-based organic antibacterial agent 1
(Apasider Clear made by Sangi Co., Ltd.)
2-methyl-[4-(methylthio) phenyl]-2-morpholino-1-propane (photopolymerization initiator) 4
(Irgacure 907 made by Ciba-Geigy Co.)
Isopropyl alcohol 100

After application of the coating agent, 150 mJ/cm² of ultraviolet rays were irradiated to the coating agent to provide a hard coat sheet having an excellent antibacterial property.

Comparative Example 1

A polyethylene terephthalate film (A4100 made by TOYOBO Co., Ltd.) having a thickness of 50 μm was used as the base sheet, and a coating agent having the following composition was applied at a thickness of 3 pm onto the base sheet by the Meyer bar.

Pentaerythritol triacrylate 100
(tri-functional acrylate)
(Aronix M-305 made by Toagosei Co., Ltd.)
Silver-based inorganic antibacterial agent carried on zirconium phosphate 0.05
(having an average particle size of 0.5 μ
(NOVARON AG300 made by Toagosei Co., Ltd.)
2-methyl-[4-(methylthio) phenyl]-2-morpholino-1-propane (photopolymerization initiator) 4
(Irgacure 907 made by Ciba-Geigy Co.)
Methylethyl ketone 100

After application of the coating agent, 150 mJ/cm² of ultraviolet rays were irradiated to the coating agent to provide a hard coat sheet.

Comparative Example 2

A polyethylene terephthalate film (A4100 made by TOYOBO Co., Ltd.) having a thickness of 50 μm was used as the base sheet, and a coating agent having the following composition was applied at a thickness of 3 μm onto the base sheet by the Meyer bar.

Pentaerythritol triacrylate 100
(tri-functional acrylate)
(Aronix M-305 made by Toagosei Co., Ltd.)
Silver-based inorganic antibacterial agent carried on zirconium phosphate 20
(having an average particle size of 0.5 μm)
(NOVARON AG300 made by Toagosei Co., Ltd.)
2-methyl-[4-(methylthio) phenyl]-2-morpholino-1-propane (photopolymerization initiator) 5
(Irgacure 907 made by Ciba-Geigy Co.)
Methylethyl ketone 100

After application of the coating agent, 200 mJ/cm² of ultraviolet rays were irradiated to the coating agent to provide a hard coat sheet.

Comparative Example 3

A polyethylene terephthalate film (A4100 made by TOYOBO Co., Ltd.) having a thickness of 50 μm was used as the base sheet, and a coating agent having the following composition was applied. at a thickness of 3 μm onto the base sheet by the Meyer bar.

Pentaerythritol triacrylate 100
(tri-functional acrylate)
(Aronix M-305 made by Toagosei Co., Ltd.)
Silver-based inorganic antibacterial agent carried on calcium phosphate 1
(having an average particle size of 1.5 μm)
(Apasider AW made by Sangi Co., Ltd.)
2-methyl-[4-(methylthio) phenyl]-2-morpholino-1-propane (photopolymerization initiator) 4
(Irgacure 907 made by Ciba-Geigy Co.)
Methylethyl ketone 100

After application of the coating agent, 150 mJ/cm² of ultraviolet rays were irradiated to the coating agent to provide a hard coat sheet.

Then, Examples 1 to 8 and Comparative Examples 1 to 3 were subjected to a characteristic test to provide results which are given in Tables 1 and 2 below.

TABLE 1

|  | Ex. 1 | Ex. 2 | Ex. 3 | Ex. 4 | Ex. 5 | Ex. 6 | Ex. 7 | Ex. 8 |
|---|---|---|---|---|---|---|---|---|
| Haze (%) | | | | | | | | |
| at initial stage | 1.06 | 2.31 | 4.52 | 1.27 | 1.30 | 1.44 | 1.21 | 1.12 |
| after wear test | 2.11 | 3.84 | 5.81 | 2.18 | 2.24 | 2.31 | 2.17 | 2.10 |
| Pencil hardness | H | H | H | H | H | H | H | HB |
| Antibacterial property | | | | | | | | |
| at initial stage | ○ | ○ | ○ | ○ | ○ | ○ | ○ | ○ |
| after durability test | ○ | ○ | ○ | ○ | ○ | ○ | ○ | — |
| Dispersability of anti-bacterial agent | | | | | | | | |
| at preparation of coating agent | ○ | ○ | ○ | ○ | ○ | ○ | ○ | ○ |
| for coating surface | ○ | ○ | ○ | ○ | ○ | ○ | ○ | ○ |

TABLE 2

|  | Co. Ex. 1 | Co. Ex. 2 | Co. Ex. 3 |
|---|---|---|---|
| Haze (%) | | | |
| at initial stage | 0.82 | 8.65 | 1.48 |
| after wear test | 1.73 | 10.43 | 2.36 |
| Pencil hardness | H | H | H |
| Antibacterial property | | | |
| at initial stage | X | ○ | ○ |
| after durability | X | ○ | ○ |

TABLE 2-continued

|  | Co. Ex. 1 | Co. Ex. 2 | Co. Ex. 3 |
|---|---|---|---|
| test Dispersability of anti-bacterial agent | | | |
| at preparation of coating agent | O | X | X |
| for coating surface | O | X | X |

For each of the characteristics, each of Examples 1 to 8 and Comparative Examples 1 to 3 was tested in the following manners:

Haze (at the initial stage): It was measured by a haze meter (made byNippon Denshoku Kogyo Co., Ltd.) according to JIS K6714.

Haze (after the wear test): The hard coat sheet was tested at a load of 250 g and at a number of rotations of 100 by a Taber wear testing machine (made by Tester Industries, Co.) having wearing wheel CS-10F according to JIS 5400 and then, the haze was measured in the same manner as at the initial stage.

Pencil hardness: It was measured in a hand scratching manner according to JIS K5400.

Antibacterial property at initial stage: Colon bacilli were inoculated into the surface of the coat layer (3 cm×3 cm) and then, the hard coat sheet was wrapped. After leaving the resulting sheet to stand for 24 hours in a desiccator with water placed therein at 27° C., the number of living colon bacilli was measured. The hard coat sheet having a reduced number of living colon bacilli was represented by O, and the hard coat sheet having a non-reduced number of living colon bacilli was represented by X.

Antibacterial property after durability test: A coated sample was thrown under a drying condition at 100° C. After a lapse of 1,000 hours, the sample was removed, and the antibacterial property was checked in the same manner as at the initial stage.

Dispersability of antibacterial agent at the preparation of the coating agent: The coating agent was prepared and left to stand for one hour. The dispersed state of the antibacterial agent in the coating agent at that time was observed. The hard coat agent including the antibacterial agent which was not settled, or which was settled, but returned to the usual dispersed state by a slight agitation, is represented by O. The hard coat agent including the antibacterial agent which was settled and could not be dispersed again, is represented by X.

Dispersability of antibacterial agent for coating surface:

The coating surface was observed. The hard coat sheet which included the lump (agglomerate) of the antibacterial agent that could be visually observed and which had a partially increased haze value to become whitened, is represented by X. The hard coat sheet including the agglomerate of the antibacterial agent that could not be visually observed, is represented by O.

As apparent from Table 1, the hard coat sheet according to the present invention has an excellent antibacterial property in addition to the scratch resistance performance, and an excellent transparency such that the haze value is equal to or lower than 5%, and equal to or lower than 10% even after the wear test.

What is claimed is:

1. A sheet comprising a transparent base sheet, and a hardened coating of a radiating-curing acrylate resin including an antibacterial agent provided on said transparent base sheet.

2. A coated sheet according to clam 1, wherein the weight ratio of said radiation-curing acrylate resin to said antibacterial agent is in a range of 100:0.1 to 100:15.

3. A coated sheet according to claim 1 or 2, wherein the average particle size of said antibacterial agent is equal to or smaller than 1 μm.

4. A coated sheet according to claim 3, wherein said antibacterial agent is an inorganic substance.

5. A coated sheet according to claim 3, further providing an adhesive agent layer provided on one side of said transparent base sheet.

6. A coated sheet according to claim 1 or 2, wherein said antibacterial agent is an inorganic substance.

7. A coated sheet according to claim 6, further providing an adhesive agent layer provided on one side of said transparent base sheet.

8. A coated sheet according to claim 1 or 2, further providing an adhesive agent layer provided on one side of said transparent base sheet.

* * * * *